US00PP18118P2

(12) United States Plant Patent
Danziger

(10) Patent No.: US PP18,118 P2
(45) Date of Patent: Oct. 9, 2007

(54) ***SUTERA* PLANT NAMED 'DANGUL16'**

(50) Latin Name: *Sutera cordata*
Varietal Denomination: DANGUL16

(75) Inventor: Gabriel Danziger, Moshav Nir-Zvi (IL)

(73) Assignee: Danziger "Dan" Flower Farm, Post Beit Dagan (IL)

( * ) Notice: Subject to any disclaimer, the term of this patent is extended or adjusted under 35 U.S.C. 154(b) by 0 days.

(21) Appl. No.: 11/392,497

(22) Filed: Mar. 30, 2006

(51) Int. Cl.
*A01H 5/00* (2006.01)

(52) U.S. Cl. ..... Plt./263
(58) Field of Classification Search ..... Plt./263
See application file for complete search history.

(56) References Cited

PUBLICATIONS

European Union Community Plant Variety Office (CPVO)—for Application No. 2005/2053 filed Oct. 26, 2005—documents include Dec. 15, 2005 print out from CPVO Official Gazette verifying application information (1 pg.) and Technical Questionnaire (5 pgs).

*Primary Examiner*—Kent Bell
*Assistant Examiner*—S. B. McCormick-Ewoldt
(74) *Attorney, Agent, or Firm*—Foley & Lardner, LLP

(57) ABSTRACT

A new and distinct *Sutera* plant named 'DANGUL16' particularly characterized by 5-petalled flowers, measuring 2.4 cm in diameter and lavender in color with a yellow-orange colored throat; vigorous growth which maintains a trailing, compact growth habit; early flowering response, suitable for use with hanging basket planters, combination planters and ground cover under full sunlight-and slight shade.

2 Drawing Sheets

Latin name of the genus and species of the claimed plant: *Sutera cordata.*
Variety denomination: 'DANGUL16'.

BACKGROUND OF THE INVENTION

The present invention relates to a new and distinct cultivar of *Sutera* plant, botanically known as *Sutera cordata,* hereinafter referred to by the cultivar name 'DANGUL16'.

*Sutera,* of the Scrophulariaceae family, consists of annuals which are grown in most climate zones in the U.S., and only in zones 9 and 10 if it is a perennial plant.

The new *Sutera* cultivar is a product of a planned breeding program conducted by the inventor, Gabriel Danziger, in Moshav Mishmar Hashiva, Israel. The objective of the breeding program is to develop a new *Sutera* variety with large, lavender flowers and a trailing, compact growth habit.

The new *Sutera* cultivar originated from a cross made in a controlled breeding program by the inventor in 2003, in Moshav Mishmar Hashiva, Israel. The female or seed parent is a *Sutera* cultivar designated 'CV-3-86' from our breeding program (unpatented). The male or pollen parent is *Sutera* cultivar designated 'OP21' from our breeding program (unpatented). The new *Sutera* cultivar 'DANGUL16' was discovered and selected by the inventor, Gabriel Danziger, as a single flowering plant within the progeny of the stated cross in a controlled environment in Moshav Mishmar Hashiva, Israel.

Asexual reproduction of the new *Sutera* cultivar by vegetative cuttings was first performed in May of 2004 in Moshav Mishmar Hashiva, Israel, and has demonstrated that the combination of characteristics as herein disclosed for the new cultivar are firmly fixed and retained through successive generations of asexual reproduction. The new cultivar reproduces true to type.

BRIEF SUMMARY OF THE INVENTION

The following traits have been repeatedly observed and are determined to be unique characteristics of 'DANGUL16', which in combination distinguish this *Sutera* as a new and distinct cultivar:

1. 5-petalled flowers, measuring about 2.4 cm in diameter and lavender in color with a yellow-orange colored throat;
2. Vigorous growth which maintains a trailing, compact growth habit;
3. Early flowering response; and
4. Suitable for use with hanging basket planters, combination planters and ground cover under full sunlight-and slight shade.

Plants of 'DANGUL16' differ from the plants of the female parent, 'CV-3-86' primarily in flower size and growth habit. Plants of 'DANGUL16' produce flowers larger in size (about 2.4 cm in diameter) than plants of 'CV-3-86' (about 1.9 cm in diameter). Plants of 'DANGUL16' have a more compact growth habit (height about 10 cm and spread about 40 cm) than plants of the 'CV-3-86' (height about 15 cm and spread about 60 cm).

Of the many commercial cultivars known to the inventor, the most similar in comparison to 'DANGUL16' is the *Sutera* cultivar 'Great Lavender' (unpatented). The new cultivar is distinguishable from 'Great Lavender' in flower and leaf size. The flower size of 'DANGUL16' is 2.4 cm and its leaves are large (length about 2.2 cm and width about 1.5 cm), whereas 'Great Lavender' flowers are 2.0 cm in size and its leaves are small (length about 1.5 cm and width about 0.7 cm).

BRIEF DESCRIPTION OF THE DRAWINGS

The accompanying photographic drawings illustrate the overall appearance of the new *Sutera* cultivar 'DANGUL16' showing the colors as true as is reasonably possible with colored reproductions of this type. Colors in the photographs may differ slightly from the color value cited in the detailed botanical description which accurately describe the color of 'DANGUL16'.

DETAILED BOTANICAL DESCRIPTION

Figure 1:
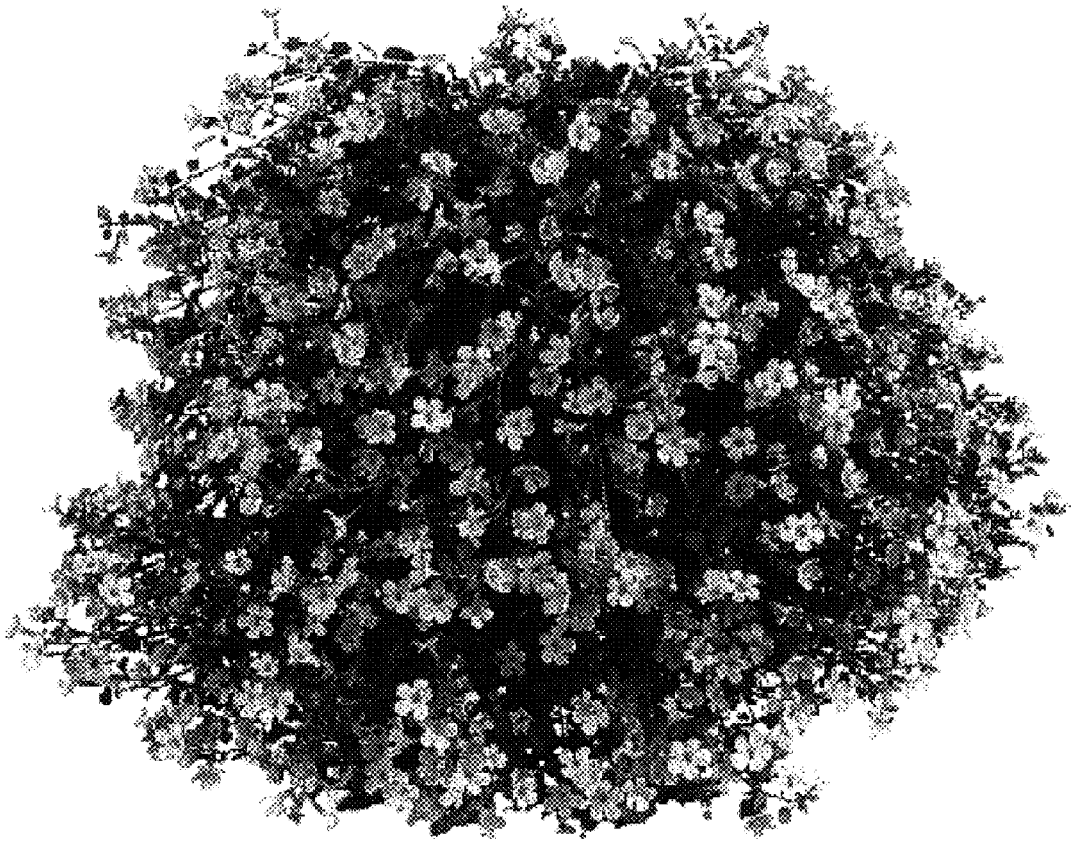
FIG. 1 shows a top view perspective of a typical 'DANGUL16' plant in a hanging basket at 3 months.
Figure 2:
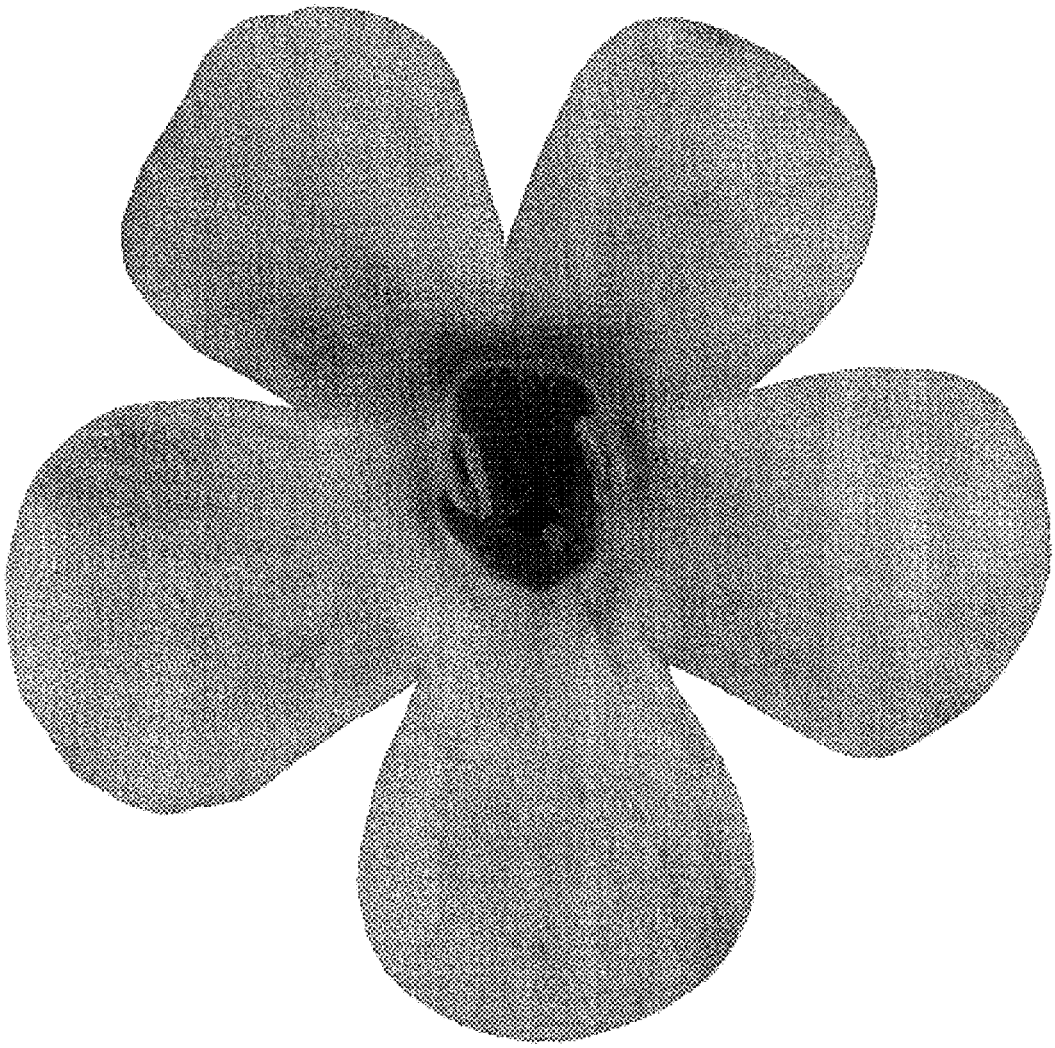
FIG. 2 shows a close-up view of the single flower of 'DANGUL16' at 3 months.

The new *Sutera* cultivar 'DANGUL16' has not been observed under all possible environmental conditions. The phenotype of the new cultivar may vary significantly with variations in environment such as temperature, light intensity, and day length without any change in the genotype of the plant.

The aforementioned photographs, together with the following observations, measurements and values describe the new *Sutera* cultivar 'DANGUL16' as grown in a greenhouse in Moshav Mishmar Hashiva, Israel, under conditions which closely approximate those generally used in commercial practice.

Color references are made to The Royal Horticultural Society Colour Chart (R.H.S.), 2001 edition, except where general colors of ordinary significance are used. Color values were taken under daylight conditions at approximately 12:00 noon in Moshav Mishmar Hashiva, Israel. The age of the plant described is 2 months.

Classification:

*Botanical.*—*Sutera cordata*

*Commercial.*—*Sutera* Scopia™ Gulliver Lavendar.

Parentage:

*Female or seed parent.*—*Sutera* cultivar designated 'CV-3-86' (unpatented).

*Male or pollen parent.*—OP21 from our breeding program (unpatented).

Optimal growth conditions:

*Light intensities.*—Full sunlight or slight shade.

*Temperature.*—Day: 20° C. to 24° C. Night: 16° C. to 20° C.

*Temperature tolerance.*—Tolerant to a low temperature of about 10° C. and a high tolerant to a high temperature of about 30° C.

*Fertilization.*—A balanced fertilizer with a level of 100 ppm Nitrogen.

*Growth regulators.*—Unnecessary.

Propagation:

*Type.*—Tip cuttings of side shoots.

*Rooting habit and description.*—Easy to root.

*Time to initiate roots.*—About 7 to 10 days at 18° C.

*Time to produce a rooted cutting.*—About 14 days at 18° C.

Plant:

*General appearance and form.*—Height: 10 cm. Spread: 40 cm.

*Shape.*—Trailing, compact growth habit.

*Winter hardiness.*—Hardy in moderate climate.

*Vigor.*—Strong.

*Strength.*—Good.

*Crop time.*—About 8 to 10 weeks for a flowering pot.

*Fragrance.*—None.

*Branching habit.*—Vigorously branched.

*Lateral branches:*

TABLE 1

| Branch characteristic | Primary | Secondary |
|---|---|---|
| Length | 40 cm. | 15 cm. |
| Diameter | 2 mm. | 1 mm. |
| Internode Length | 2 cm. | 1.5 cm. |
| Texture | Slightly rough | Slightly rough |
| Pubescence | Present | Present |
| Color | Green, RHS 137C | Green, RHS 137C |

Foliage:

*Arrangement and attachment.*—Opposite, petiolate.

*Leaf length.*—2.2 cm.

*Leaf width.*—1.5 cm.

*Overall shape of leaf.*—Rhomboidal.

*Apex shape.*—Acute.

*Base shape.*—Acute.

*Margin.*—Dentate.

*Texture (both surfaces).*—Slightly velvety.

*Pubescence (both surfaces.).—Slightly present.*

*Color of upper surface.*—Mature leaf: Yellow-Green, RHS 147A. Immature leaf: Green, RHS 137B.

*Color of lower surface.*—Mature leaf: Green, RHS 137B. Immature leaf: Green, RHS 137C.

*Venation.*—Pattern: Palmate. Color: Upper surface: Yellow-Green, RHS 147A. Lower surface: Green, RHS 137B.

*Petiole.*—Length: 4 mm. Diameter: 1 mm. Color: Yellow-Green, RHS 147A.

*Leaf fragrance.*—None.

Flower description:

*Natural flowering season.*—All year round in moderate climate. Flowering occurs year round outdoors in Israel.

*Flowering response time.*—About 4 weeks from planting.

*Flowering longevity.*—On the plant: Flowering of a single flower lasts for 7 days.

*Flower fragrance.*—None.

*Quantity of flowers and buds per plant.*—Approximately 200.

*Flower bud (about 2 days prior to opening).*—Shape: Spatulate. Length: 18 mm. Diameter: 7 mm. Texture: Velvety. Color: Lavender (violet-blue group), RHS 92B.

*Flower type.*—Solitary, auxillary.

*Flower form.*—Salverform.

*Flower symmetry.*—Bilateral symmetry.

*Orientation at opening.*—Slanted upward and outward.

*Corolla size.*—Diameter (spread): 2.4 cm. Diameter at lobes: 24 mm. Overall flower height: 14 mm. Length of corolla tube: 12 mm. Diameter of corolla tube: 1 mm.

*Petals.*—Quantity: 5. Length: 9 mm. Width: 8 mm. Overall shape: Rounded and gameopetalous. Apex: Rounded. Base: Fused. Margin: Entire. Texture (upper and lower surfaces): Slightly velvety. Color: Upper surface, when opened: Lavender (violet-blue group), RHS 91A. Upper surface, opened flower: Lavender (violet-blue group), RHS 91B. Lower surface, when opening: Lavender (violet-blue group), RHS 91B. Lower surface, opening flower: Lavender (violet-blue group), RHS 91C. Corolla throat color: Yellow-orange, RHS 21A.

*Calyx.*—Sepals: Quantity: 5 Length: 4 mm. Width: 1 mm. Overall shape: Linear. Apex: Acute. Base: Fused. Margin: Entire. Texture: Upper surface: Velvety. Lower surface: Velvety. Upper surface color: Green, RHS 137C. Lower surface color: Green, RHS 137C. Anthocyan pigmentation of calyx limb: Absent.

*Pedicel.*—Aspect: Slanted upward. Length: 9 mm. Diameter: 1 mm. Angle: About 45°. Texture: Velvety. Color: Green, RHS 137C.

Reproductive organs:

*Androecium.*—Stamen: Number: 4. Arrangement: Didynamous. Type: Basifixed. Dehiscence of stamens: Extrorse. Color: Yellow-orange, RHS 21A. Anthers: Shape: Cylinder. Length: 1 mm. Color: Yellow-orange, RHS 21A. Filaments: Length: About 10 mm. Color: RHS 150D yellow-green group. Pollen: Amount: Moderate. Color: Yellow-orange, RHS 21A. Pollination requirements: Young flowers, vital pollen, and receptive, open stigma.

*Gynoecium.*—Pistils: Quantity: 1. Length: About 13 mm. Stigma: Shape: Undulate. Width: About 0.5 mm. Color: Yellow-Green, RHS N145C. Style: Shape: Terete. Length: About 11 mm. Ovary: Shape: Ellipsoid. Position: Superior. Length: About 2 mm. Width: About 1 mm. Color: Green, RHS 139B.

Seeds:

*Quantity per fruit.*—About 20.

*Shape.*—Elliptic.

*Length.*—About 1 mm.

*Width.*—About 0.5 mm.

*Texture.*—Rough.

*Color.*—Greyed-orange, RHS 165B.

Fruit:

*Type.*—Capsule.

*Shape.*—Ellipsoid.

*Length.*—About 4 mm.

*Width.*—About 2 mm.

*Texture.*—Rugose.

*Color.*—Greyed-Orange, RHS 165B.

Disease/pest resistance: No information is currently available.

Disease/pest susceptibility: No information is currently available.

I claim:

1. A new and distinct *Sutera* plant named 'DANGUL16', substantially as illustrated and described herein.

* * * * *